(12) United States Patent
Shea et al.

(10) Patent No.: US 8,820,929 B2
(45) Date of Patent: Sep. 2, 2014

(54) REAL-TIME MEASUREMENT/DISPLAY/RECORD/PLAYBACK OF WAVEFRONT DATA FOR USE IN VISION CORRECTION PROCEDURES

(75) Inventors: William Shea, Pleasanton, CA (US); Brad Nordstrom, Alameda, CA (US); Brad Chew, San Ramon, CA (US); Yan Zhou, Pleasanton, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 0 days.

(21) Appl. No.: 13/034,648

(22) Filed: Feb. 24, 2011

(65) Prior Publication Data

US 2011/0242483 A1      Oct. 6, 2011

Related U.S. Application Data

(60) Continuation-in-part of application No. 12/790,301, filed on May 28, 2010, now Pat. No. 8,579,437, which is a division of application No. 11/761,890, filed on Jun. 12, 2007, now Pat. No. 7,815,310, which is a continuation-in-part of application No. 11/335,980, filed on Jan. 20, 2006, now Pat. No. 7,445,335.

(51) Int. Cl.

| | |
|---|---|
| *A61B 3/10* | (2006.01) |
| *A61B 3/14* | (2006.01) |
| *A61B 3/00* | (2006.01) |
| *A61B 3/103* | (2006.01) |
| *A61F 9/007* | (2006.01) |
| *A61B 3/15* | (2006.01) |

(52) U.S. Cl.
CPC ............... *A61B 3/1015* (2013.01); *A61F 9/007* (2013.01); *A61B 3/145* (2013.01); *A61B 3/0058* (2013.01); *A61B 3/1035* (2013.01); *A61B 3/152* (2013.01)
USPC .......................................... 351/205; 351/246

(58) Field of Classification Search
USPC .......................... 351/200, 205, 206, 209, 246
See application file for complete search history.

(56) References Cited

U.S. PATENT DOCUMENTS

| | | | |
|---|---|---|---|
| 4,141,652 | A | 2/1979 | Feinleib |
| 5,164,578 | A | 11/1992 | Witthoft et al. |

(Continued)

FOREIGN PATENT DOCUMENTS

| | | | |
|---|---|---|---|
| EP | 1 967 864 A2 | | 9/2008 |
| GB | 2399627 A | * | 9/2004 |

(Continued)

OTHER PUBLICATIONS

PCT Search Report, Feb. 24, 2012.

(Continued)

*Primary Examiner* — James Greece

(74) *Attorney, Agent, or Firm* — Kilpatrick Townsend & Stockton LLP

(57) ABSTRACT

One embodiment is an apparatus/system for providing feedback to a procedure. The apparatus includes a real time wavefront sensor for measuring the wavefront of an optical beam, a real time video camera for capturing a scene where the optical beam comes from, a computer for processing the captured wavefront data and synchronizing the data with the video and outputting the synchronized information to a display, and a display for simultaneously displaying the synchronized wavefront and video information. Another embodiment of the present invention is a method for providing feedback to a procedure. The method involves the steps of measuring the wavefront of an optical beam with a real time wavefront sensor; capturing a video of a scene from which the optical beam comes; processing the captured wavefront data and synchronizing it with the video; and simultaneously displaying the wavefront information with the video on the same display screen.

24 Claims, 2 Drawing Sheets

(56) References Cited

U.S. PATENT DOCUMENTS

| | | | |
|---|---|---|---|
| 5,345,281 | A | 9/1994 | Taboada et al. |
| 5,568,208 | A | 10/1996 | Van de Velde |
| 5,651,600 | A | 7/1997 | Dorsey-Palmateer |
| 5,777,719 | A | 7/1998 | Williams |
| 6,199,986 | B1 | 3/2001 | Williams et al. |
| 6,376,819 | B1 | 4/2002 | Neal et al. |
| 6,409,345 | B1 | 6/2002 | Molebny |
| 6,530,917 | B1 | 3/2003 | Seiler |
| 6,578,963 | B2 | 6/2003 | Pettit |
| 6,595,642 | B2 | 7/2003 | Wirth |
| 6,685,317 | B2 | 2/2004 | Su et al. |
| 6,709,108 | B2 | 3/2004 | Levine et al. |
| 6,736,510 | B1 | 5/2004 | Van Heugten |
| 6,781,681 | B2 | 8/2004 | Horwitz |
| 6,784,408 | B1 | 8/2004 | Cheung |
| 6,791,696 | B1 | 9/2004 | Fantone et al. |
| 6,793,654 | B2 | 9/2004 | Lemberg |
| 6,827,444 | B2 | 12/2004 | Williams et al. |
| 6,880,933 | B2 | 4/2005 | Davis |
| 6,890,076 | B2 | 5/2005 | Roorda |
| 6,910,770 | B2 | 6/2005 | Campbell |
| 6,932,475 | B2 | 8/2005 | Molebny |
| 6,964,480 | B2 | 11/2005 | Levine |
| 7,284,862 | B1 | 10/2007 | Lai |
| 7,414,712 | B2 | 8/2008 | Yoon |
| 7,445,335 | B2 | 11/2008 | Su |
| 7,554,672 | B2 | 6/2009 | Greenaway |
| 7,665,846 | B2 | 2/2010 | Campin et al. |
| 7,771,048 | B2 | 8/2010 | Dai et al. |
| 7,815,310 | B2 | 10/2010 | Su |
| 7,988,291 | B2 | 8/2011 | Ianchulev |
| 8,002,410 | B2 | 8/2011 | Shea |
| 8,356,900 | B2 | 1/2013 | Zhou et al. |
| 8,454,162 | B2 | 6/2013 | Zhou et al. |
| 8,579,437 | B2 | 11/2013 | Su et al. |
| 8,591,027 | B2 | 11/2013 | Su et al. |
| 2001/0019361 | A1* | 9/2001 | Savoye ......................... 348/222 |
| 2002/0159030 | A1 | 10/2002 | Frey et al. |
| 2002/0169441 | A1 | 11/2002 | Lemberg |
| 2003/0038921 | A1 | 2/2003 | Neal et al. |
| 2003/0053031 | A1 | 3/2003 | Wirth |
| 2003/0063257 | A1 | 4/2003 | Molebny |
| 2003/0086063 | A1* | 5/2003 | Williams et al. ............... 351/221 |
| 2003/0174281 | A1* | 9/2003 | Herekar et al. ................ 351/200 |
| 2003/0223037 | A1* | 12/2003 | Chernyak ...................... 351/209 |
| 2004/0004696 | A1 | 1/2004 | Davis et al. |
| 2004/0008321 | A1 | 1/2004 | Saigussa et al. |
| 2004/0156015 | A1 | 8/2004 | Campbell |
| 2004/0239876 | A1 | 12/2004 | Levine |
| 2005/0094100 | A1 | 5/2005 | Ross et al. |
| 2005/0134851 | A1 | 6/2005 | Murphy |
| 2006/0077347 | A1 | 4/2006 | Liang |
| 2007/0171366 | A1 | 7/2007 | Su et al. |
| 2008/0284979 | A1* | 11/2008 | Yee et al. ...................... 351/209 |
| 2009/0185132 | A1 | 7/2009 | Raymond |
| 2010/0110379 | A1 | 5/2010 | Zhou |
| 2010/0165290 | A1 | 7/2010 | Shea |
| 2010/0231858 | A1 | 9/2010 | Su |
| 2011/0164220 | A1 | 7/2011 | Su et al. |
| 2012/0026466 | A1 | 2/2012 | Zhou et al. |
| 2012/0069303 | A1 | 3/2012 | Seesselberg |
| 2012/0188506 | A1 | 7/2012 | Zhou et al. |
| 2012/0238904 | A1 | 9/2012 | Manns et al. |
| 2012/0268717 | A1 | 10/2012 | Zhou et al. |
| 2013/0265541 | A1 | 10/2013 | Zhou |

FOREIGN PATENT DOCUMENTS

| | | |
|---|---|---|
| WO | PCT/EP2003/008787 | 8/2003 |
| WO | 03/073121 A1 | 9/2003 |
| WO | 2007/087058 A1 | 8/2007 |

OTHER PUBLICATIONS

PCT/EP2003/008787 English Translation.

"Hands-on Internet Photodiode Sensing Using the Internet, Cyril Bateman Has Been Examining the Benefits of Transimpedance Amplifiers Over Transconductance Amplifiers When Measuring Light Using a Photodiode," Electronics World, Nexus Media Communications, Swanley, Kent GB, vol. 106, No. 1767, pp. 210-215.

Abado, Shaddy, "Two-dimensional high-bandwidth Shack-Hartmann wavefront sensor: design guidelines and evaluation testing," Optical Engineering, 2010, vol. 49, No. 6, pp. 064403.

Abado, Shaddy, "Designing and testing a high-bandwidth 2-D wavefront sensor for Aero-optics," Proc. SPIE, Advanced Wavefront Control: Methods, Devices, and Applications VII, Aug. 11, 2009, vol. 7466.

De Lima Monteiro, D.W. et al., "Fast Hartmann-Shack Wavefront Sensors Manufactured in Standard CMOS Technology," IEEE Sensors Journal, IEEE Service Center, New York, NY, Oct. 1, 2005, vol. 5, No. 5, pp. 976-982.

Rana, N.K., "A Non-contact Method for Rod Straightness Measurement Based on Quadrant Laser Sensor," Industrial Technology, 2006, ICIT 2006, IEEE International Conference on IEEE, PI, Dec. 1, 2006, pp. 2292-2297.

"Transimpedanzverstärker," Wikipedia, Apr. 25, 2012, retrieved from the Internet: http://de.wikipedia.org/w/index.php?title-Transimpedanzverst%C3%A4rker&oldid=102459149 [retrieved in Jan. 31, 2014] section "Anwendung".

Vera-Marquina, A. et al., "Quadrant photodiode for electronic processing," Proc. SPIE 7419, Infrared Systems and Photoelectronic Technology IV, 74190Z, vol. 7419, Aug. 2, 2009, pp. 74190Z-3 to 74190Z-4.

Brockington, Samuel et al., "Plasma density gradient measurement using laser deflection," Review of Scientific Instruments, AIP, Melville, NY, vol. 76, No. 6, Jun. 6, 2005, 063503, 7 pages.

Dave, T., "Wavefront aberrometry Part 1: Current Theories and Concepts", Optometry Today, Nov. 19, 2004, pp. 41-45.

Ginis, H.S. et al., Variability of wavefront aberration measurements in small pupil sizes using a clinical Shack-Hartmann aberrometer, BMC Ophthalmology, Feb. 11, 2004, 4:1.

Goodman, J., "Introduction to Fourier Optics, Second Edition," The McGraw-Hill Companies, Inc., 1998, pp. 232-233, 273-274.

Liang, J. et al., "Objective measurements of wave aberrations of the human eye with the use of a Hartmann-Shack wavefront sensor," J. Opt. Soc. Am. A., vol. 11, No. 7, Jul. 1994, pp. 1949-1957.

Wei, Xin et al., "Design and validation of a scanning Shack-Hartmann aberrometer for measurements of the eye over a wide field of view," Optics Express, OSA, Jan. 18, 2010, vol. 18, No. 2, pp. 1-10.

Widiker, J. et al., "High speed Shack-Hartmann wavefront sensor design with commercial off-the-shelf optics," Applied Optics, vol. 45, Jan. 2006, pp. 393-395.

* cited by examiner

REAL-TIME MEASUREMENT/DISPLAY/RECORD/ PLAYBACK OF WAVEFRONT DATA FOR USE IN VISION CORRECTION PROCEDURES

RELATED APPLICATIONS

This application is a continuation-in-part of application Ser. No. 12/790,301 entitled Adaptive Sequential Wavefront Sensor With Programmed Control filed May 28, 2010 which is a divisional application of application Ser. No. 11/761,890 entitled Adaptive Sequential Wavefront Sensor, filed Jun. 12, 2007 now U.S. Pat. No. 7,815,310, issued Oct. 19, 2010, which is a continuation-in-part of application Ser. No. 11/335,980 entitled Sequential Wavefront Sensor, filed Jan. 20, 2006 now U.S. Pat. No. 7,445,335, issued Nov. 4, 2008, all of which are incorporated by reference for all purposes.

TECHNICAL FIELD

One or more example embodiments relate generally to wavefront sensor(s) for use in vision correction procedures. In particular, one example embodiment is an apparatus/system and a method for real-time measurement/display/record/playback of wavefront data synchronized with/to a video "movie", to provide real time feedback to a vision correction procedure.

BACKGROUND

A wavefront sensor is a device for measuring the aberrations of an optical wavefront. Wavefront sensors have been used for eye aberration measurement by directing a narrow beam of light to the retina of an eye and sensing the optical wavefront coming out from the eye. For a relaxed emmetropic eye or a relaxed eye with aberrations completely corrected, the optical wavefront coming out from the eye is planar. If, on the other hand, the eye has optical aberrations, the wavefront coming out from the eye in a relaxed state will depart from being planar.

Traditional vision diagnostic, vision corrective and surgical refractive procedures, including auto-refraction, standard eye wavefront measurement, phoropter test, LASIK (Laser Assisted In-Situ Keratomileusis), LTK (Laser Thermokeratoplasty), SBK (Sub-Bowmans Keratomileusis), IntraLASIK (Intra-stromal corneal lenticule extraction), PRK (photorefractive keratectomy), LASEK (Laser Assisted Sub-Epithelium Keratomileusis), IOL (Intraocular lens, including multi-focal, accommodating and toric IOL) implantation, corneal onlay/inlay implantation/positioning, RK (Radial keratotomy), LRI (Limbal Relaxing Incision), CRI (Corneal Relaxing Incision), and AK (Arcuate Keratotomy), are generally conducted without any continuous wavefront measurement result being displayed in real time to the clinical practitioner to show the effect of the correction in real time (see for example U.S. Pat. No. 6,271,914, U.S. Pat. No. 6,271,915, U.S. Pat. No. 6,460,997, U.S. Pat. No. 6,497,483, and U.S. Pat. No. 6,499,843). Although wavefront sensors have been used to measure the refractive errors and higher order aberrations of the eye before, during, and after the dynamic vision correction process, these devices generally only produce a static snapshot display of the wavefront map of the measurement, thereby potentially missing information vital to the practitioner for optimization of the optical outcome.

Overview

One embodiment is an apparatus/system for providing feedback to a vision correction procedure comprising a real time wavefront sensor for measuring the wavefront characteristics from a biological eye; a real time video camera for capturing digital images and/or recording video movies of the eye; a computer with a digital video recorder for enabling synchronized data processing, real time display, recording, and playback of both the recorded wavefront data/results and the recorded video movie of the eye; and a display connected to the computer for simultaneously displaying on the same screen the processed wavefront result and the video of the eye image.

Another embodiment is a method for providing feedback to a vision correction procedure, comprising the steps of measuring the optical wavefront from an eye with a real-time wavefront sensor; capturing and/or recording video movies of the eye with a real time video camera; processing the wavefront data and the video data with a computer having a digital video recorder to enable synchronized display, and/or recording, and/or playback of both the wavefront information and the video movie of the eye; and displaying simultaneously on the same screen or on more than one (separate) screens (heads up display in one or each ocular, for example) the processed wavefront result and the video of the eye image.

In one example embodiment, the wavefront data is captured on a frame-by-frame basis real-time in synchronization with the real time video-movie of the eye, and to display both on the same or multiple monitor(s).

In another example embodiment, Digital Video Recorder (DVR) capabilities are included so that the wavefront measurement parameters can be reviewed (rewound and played back) as a synchronized movie with the video-movie of the eye during and/or after the vision correction procedure.

DETAILED DESCRIPTION

Figure 1:
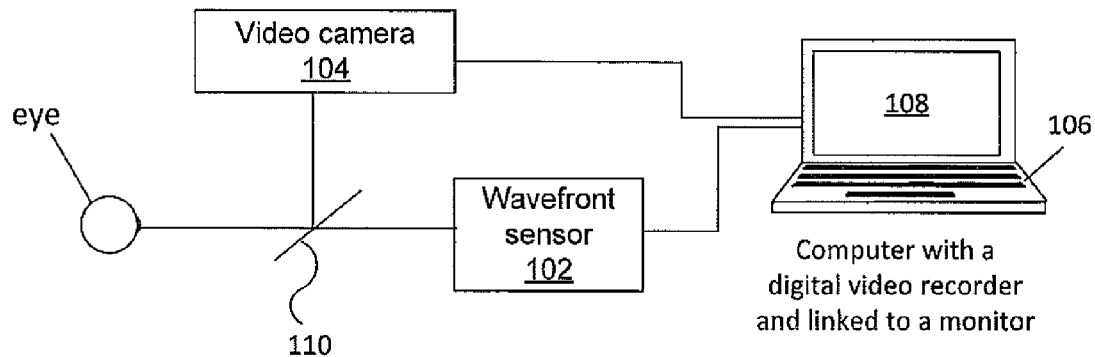
FIG. 1 shows a schematic diagram of an example apparatus/system embodiment comprising a real time wavefront sensor, a real time video camera for imaging an eye, and a computer that contains a digital video recorder and is linked to a monitor.

Conventional wavefront sensors for human eye wavefront characterization are generally designed to take a snap shot or several snap shots of a patient's eye wavefront with room lighting turned down or off. Such a wavefront sensor cannot provide continuous real time wavefront measurement results for real time feedback, especially if it is to be integrated with an ophthalmic surgical microscope with the illumination light and/or room lights turned on. For vision correction procedures, vision correction clinicians/surgeons could advantageously use a real time display of the wavefront measurement results and hence a feedback as the vision correction procedure is being performed. In addition, most surgeons could also advantageously use that the real time wavefront data to be displayed in real time is synchronized and superimposed onto a real time video display/movie of the eye from which the wavefront is associated, with the overlaid wavefront data being shown in a qualitative or a quantitative or a combined qualitative/quantitative manner.

Furthermore, in order to perform the vision correction procedures more effectively, surgeons not only need to see the real-time wavefront data with video, but also need to rewind/ replay recent segments to review a procedural step, determine how to proceed with the correction, or pause to maintain a specific point in time as a reference, for example. So far, these issues have not been adequately addressed.

In the following an apparatus/system and a method to realize real time wavefront measurement and display as well as real time display/record/playback of wavefront data in synchronization with a real time eye video display/movie is described.

In accordance with one or more example embodiments, an apparatus/system and a method for providing feedback to a vision correction procedure is disclosed. The apparatus is characterized with a real time wavefront sensor, a real time video camera, and a computer that has a digital video recorder, and a display that is linked to the computer. The method is characterized with collecting the wavefront data from an eye with a real time wavefront sensor, capturing/recording a video movie of the eye with a video camera, processing the measured wavefront data from the eye with a computer to extract the most desired information in real time for superimposing the wavefront information to the recorded video movie of the eye, and displaying both the wavefront information and the eye video on a monitor or multiple monitors linked to the computer.

One feature of an example embodiment is that the real time wavefront information and the real time eye video movie information simultaneously but respectively collected by the wavefront sensor and the eye video camera are captured and/or recorded in synchronization in a stream manner. Another feature of an example embodiment is that the collected information is processed in real time and converted into the desired format for either a real time display or a playback on the same monitor(s). Still another feature of the example embodiment is that the information to be displayed on a monitor can be determined by the end user per the user's preference.

FIG. 1 shows a schematic diagram of an apparatus/system example embodiment that comprises a real time wavefront sensor 102, a real time video camera 104, a computer 106 that is linked to the wavefront 102 sensor and the video camera 104, a display/monitor 108 that is linked to the computer 106 and a beam splitter 110.

Figure 2:
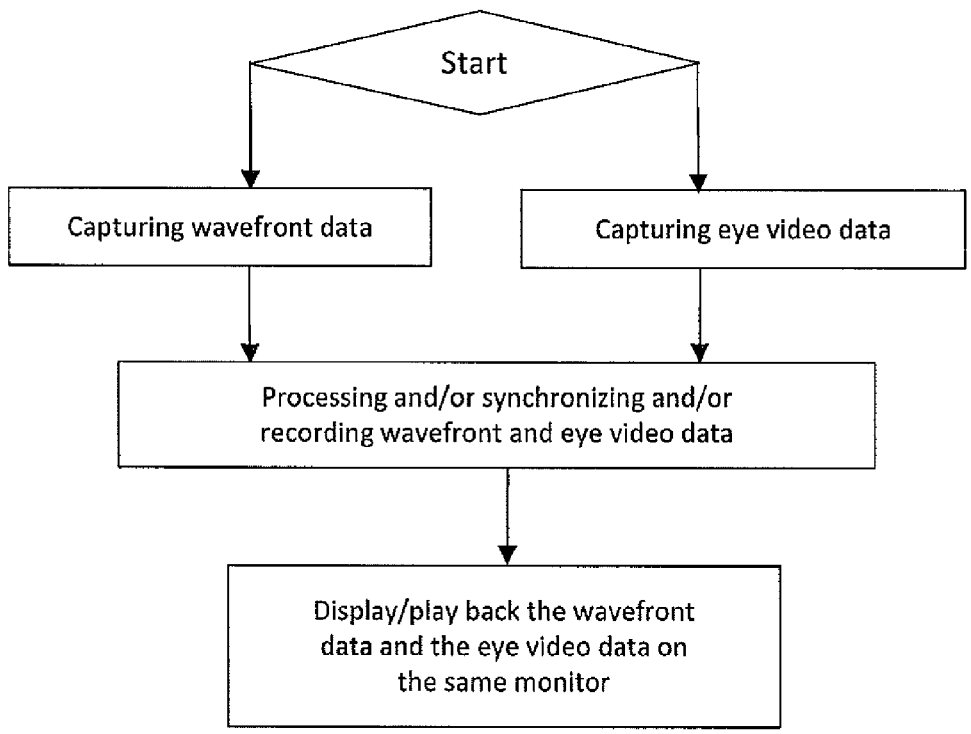
FIG. 2 shows an example flowchart of steps performed by an example embodiment.

FIG. 2 shows an example method embodiment with the steps performed. The real time wavefront sensor and the real time video camera simultaneously capture their respective data and feed the data to a computer. The beam splitter is used to direct part of the light from the eye to the video camera and another part of the light from the eye to the wavefront sensor. The beam splitter and the video camera can be embedded inside the wavefront sensor module. The computer processes the data in real time and converts the data into a desirable format for display.

In an example embodiment, the video camera and wavefront sensor are coupled to a computer and interfaced using standard off-the-shelf software compilers, UI builders, services, and drivers such as, for example, Microsoft Visual Studio Professional and the Microsoft DirectShow application programming interface (API), which is a media streaming architecture for Microsoft Windows, so that the software receives a continuous stream of data from both the video camera and wavefront sensor hardware.

The wavefront measurements can be captured on a frame-by-frame basis, similar to a video camera capturing attributes of a visual scene (e.g. color, brightness, action etc.) on a frame-by-frame basis in real-time, and be synchronized with the video-movie of the eye.

The wavefront data stream represents real-time wavefront measurement values and the camera data stream represents real-time camera frames (i.e. a "movie"). The real time wavefront measurement values are received asynchronously relative to the real-time camera frames. The software converts the wavefront stream into computer graphics which are synchronized and blended with the camera frames and displayed as a composite "movie" on the computer display that is synchronized to the real-time activity performed by the surgeon.

In an example embodiment, the wavefront sensor measurement values are converted into computer graphics in the shape of circles or ellipses which are typical representations of spherical and cylindrical refractive errors which are well understood by vision correction practitioners. These computer graphics are superimposed over the image of the biological eye as depicted below in FIG. 3. This composite "movie" is buffered so the surgeon can review (i.e. "replay") this movie at-will during and/or after the surgery.

The computer is linked to a monitor that can display the wavefront measurement result and the video movie of the biological eye simultaneously. The monitor can be part of the computer (such as in the case of a laptop) or a separate monitor or a number of monitors mutually linked among one another.

The wavefront attributes can show the optical error present in the biological eye optics system so a clinician can correct that error(s) real-time during a surgery or an examination of the eye. Without the real-time quality of the current disclosure, the clinician can only take a snapshot (single, static frame) of these attributes, which slows down each corrective adjustment significantly and allows the monitored variables to change measurably in-between snapshots (e.g. patient eye movement, tear build-up, etc.).

In addition to this real-time display benefit, this example embodiment provides Digital Video Recorder (DVR) capabilities so the parameters can be reviewed (played back) as a movie during and/or after the surgery or examination. This DVR capability allows attribute values to be examined over time, for correction during or after surgery, and for training purposes to improve surgical techniques, or instruct medical students.

It should be noted that the video camera can be a monochrome/black-white camera or a color camera. The spectral response of the video camera can cover the visible as well as the near infrared range. The camera can have zoom in and zoom out function so that the surgeon or clinician can select the digital magnification of the video image displayed. The displayed image of the eye can also be flipped or rotated to orient the surgeon's view. In an example embodiment a USB camera, model UI-2230SE-M manufactured by IDS, was utilized to form the image depicted in FIG. 3

The display can be a built-in heads up display or a micro display in the ocular path of a surgical microscope. The wavefront result and eye video movie can be played back on demand, i.e. paused during surgery and played back or afterwards. The eye video movie can be used to provide ability to identify any particular registration mark(s) manmade or natural landmark(s) for intra ocular lens (IOL) alignment, and the real time wavefront sensor measurement result can be used to compare the optical alignment or visual alignment to the physical alignment. Furthermore, the video and/or wavefront data can be used to determine key events during the procedures to aid the clinician, such as alignment to eye, eye tracking, whether the eye lid is closed, or whether an irrigation event is recommended, or a variety of other metrics.

The optical wavefront is scanned/sampled in real-time, and digitized. These digital samples are analyzed to obtain metrics such as wavefront aberrations/distortions. These metrics are used to compute optical refractive errors, typically rendered in a wavefront map and/or units of diopter errors of different orders of wavefront aberrations. The metrics are displayed and/or saved real-time in files on a persistent storage device, in part to support the DVR capability. The metrics are synchronized with the recorded video movie of the eye (a target of interest). Through user interaction with DVR controls (e.g. scan, playback, rewind, etc.), historical metrics are examined and can be used as feedback for current/future corrective eye procedures.

Figure 3:
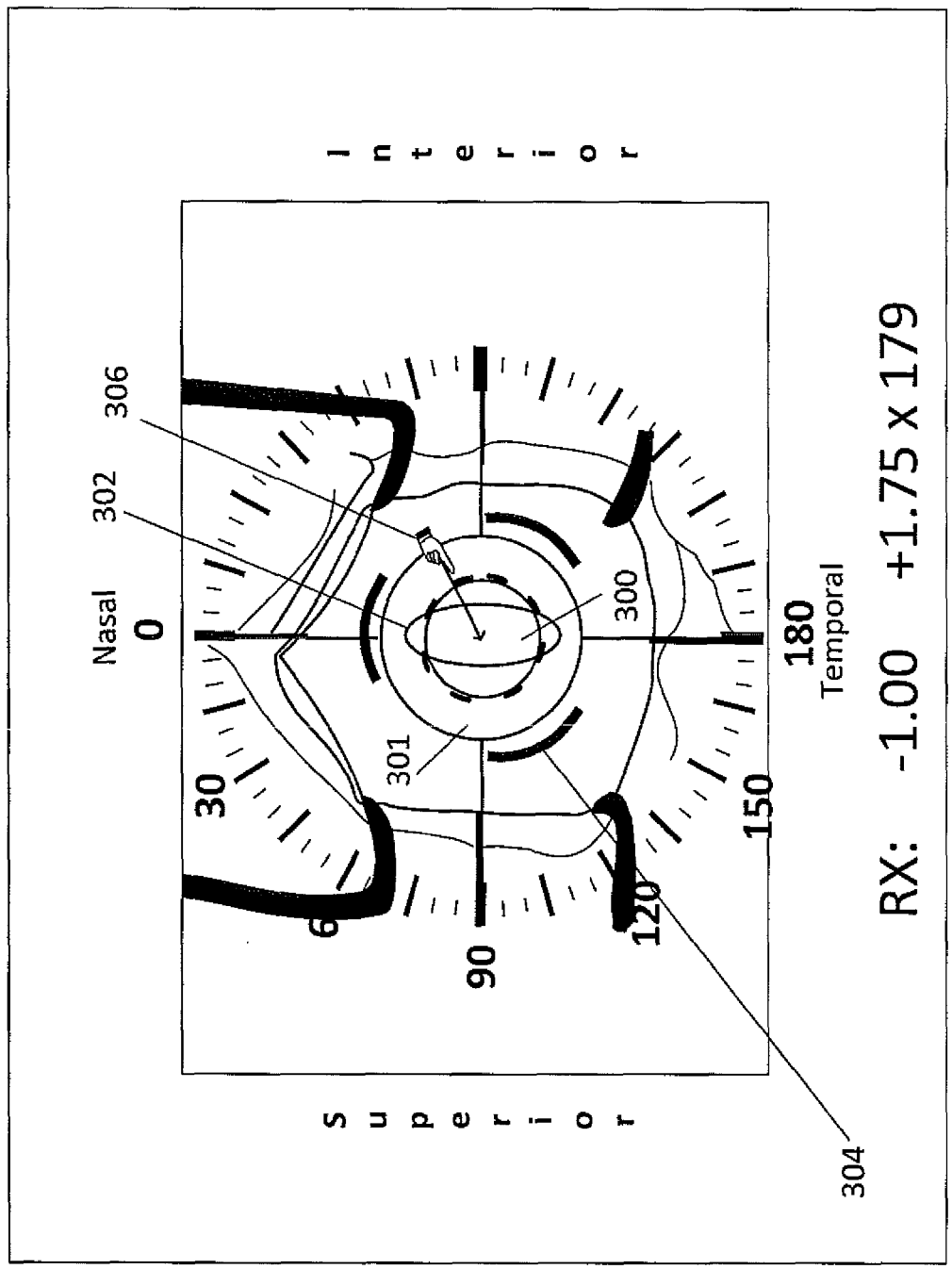
FIG. 3 depicts a screen shot of a display produced by an example embodiment.

FIG. 3 is a screen shot depicting computer graphics obtained from the wavefront sensor superimposed over a video frame of the biological eye. In FIG. 3 a computer graphic of an ellipse 302 converted from the wavefront stream is overlaid on the image of the biological eye output from the video camera. As described in U.S. patent application Ser. No. 12/609,219 entitled Optimizing Vision Correction Procedures, which has been incorporated by reference, the wavefront sensor measures the local tilt of a sampled subwavefront to show clearly the predominant feature(s) of wavefront aberration component(s), thus enabling the vision correction practitioner or the refractive surgeon to fine tune the vision correction procedure and minimize the remaining wavefront aberration(s) in real time.

In terms of sampling and displaying the real time wavefront measurement result, sampling around an annular ring enables display of the local tilt of the sampled subwavefronts on a monitor in the form of a 2D centroid data point pattern, which can be fitted to a circle or an ellipse or a straight line, thus directly indicating the two major refractive errors, namely spherical and cylindrical refractive errors, as well as the axis of the cylinder/astigmatism, or fitted to a cardioid for coma or other higher order non-symmetrical forms. As a result, a refractive surgeon can easily understand the wavefront measurement result and fine tune the vision correction accordingly.

Returning to FIG. 3, bars 304 represent confidence indicators that the eye is aligned, and wavefront data is "qualified". If the metrics for proper alignment with the wavefront sensor are not met the green bars disappear. If the wavefront sensor is out of alignment then the measurements will not be accurate and the wavefront data is not "qualified.

The hand 306 is a directional "guide" telling the clinician which way to move the patient/scope for better alignment.

The bottom numbers in FIG. 3 represent the quantified refraction in prescription manner and plus cylinder. The clinician can opt to change to refraction vs. Rx and plus cylinder versus negative cylinder. The labels on the video border represent the patient's orientation to the scope/clinician and can be rotated/changed The display can be further customized by the clinician in terms of lens prescription and/or the eye refractive error and/or end point indicators such as emmetropia. The computer can also process the wavefront sensor data to provide additional information on the state of the eye, such as tear film coverage or dry eye condition and remind the surgeon to irrigate the eye. The display can also provide other information that can be extracted by the computer from the wavefront and eye video data, such as a 2D topography map of the eye wavefront.

Additionally, the display can be configured/re-configured by the clinician to orient the display, camera, or through software the video to their preferred orientation. The clinician can also select the manner in which the qualitative and/or quantitative data is presented. These can include diopter values as either refraction or prescription; the qualitative display could be selected to show an ellipse and/or a circle to represent sphere and/or cylinder; a line intersecting the ellipse could represent the axis of astigmatism or the clinician could opt to have the refractive data presented/displayed as a 2D topography map.

The display depicted in FIG. 3 results in many advantages to a surgeon performing an ophthalmic procedure. Some of which are to let the surgeon know if the eye is aligned well enough with the wavefront sensor (with the help of a guidance circle 304 drawn on the screen so that the surgeon can position the patient eye to be co-centered with the drawn circle), to provide a confidence indicator to let the surgeon know if the wavefront result is "qualified", to let the surgeon see the effect of surgical tool(s) getting into the light path and interfering with the desired wavefront result, to let the surgeon see the effect of water irrigation onto the eye, to guide the surgeon in rotating an implanted Toric intraocular lens (IOL) to correct astigmatism, to directly show the wavefront measurement result in terms of diopters in sphere and cylinder as the correction is done both qualitatively and quantitatively, to allow the surgeon to see if there is an air bubble or remains of fractured or ruptured eye lens material still inside the eye bag that may affect the wavefront measurement result and so on.

In addition to vision correction procedures, the example embodiments can also be applied to lens making, air turbulence monitoring and wavefront correction, as well as other adaptive optics devices and systems. Additionally, the present embodiments could be applied to other devices, such as OCT, femtosecond laser, LASIK; or Doppler/radar/resonance or other devices that produce information not visible to the human eye, but could correlate that information to the physical item/human being "measured".

Although various embodiments that incorporate the teachings of the present invention have been shown and described in detail herein, those skilled in the art can readily devise many other varied embodiments that still incorporate these teachings.

Various example embodiments have been described above. Alternatives and substitutions will now be apparent to persons of skill in the art. Accordingly, it is not intended to limit the invention except as provided by the appended claims.

What is claimed is:

1. An apparatus for providing feedback during a vision correction procedure comprising:
   a real-time wavefront sensor configured to receive, during the vision correction procedure, an optical wavefront from a biological eye to measure aberrations, in real-time, of the optical wavefront;
   a real-time video camera configured to collect real-time video movie information, on a frame-by-frame basis, of the biological eye during the vision correction procedure and while the wavefront sensor is measuring the aberrations of the optical wavefront, with the video movie capturing one or more state(s) of the biological eye including intra ocular lens (IOL) alignment to registration marks, eyelid closure, irrigation, air bubbles, light path interference and tear build-up occurring during the vision correction procedure;
   a computer system, coupled to the real-time wavefront sensor and real-time video camera, with the computer system configured to store measured aberrations of the optical wavefront and collected real-time video movie information and configured to enable synchronized data processing, recording, display and playback of both stored measured aberrations of the optical wavefront and stored video movie information of the biological eye; and
   a display, connected to the computer, configured to simultaneously display, in real-time or in playback mode, aberrations of the optical wavefront measured at a particular time during the vision correction procedure and a frame of the video movie information of the biological eye collected at the particular time to allow correlation of aberrations of optical wavefront data measured at the particular time with one or more state(s) of the biological eye including intra ocular lens (IOL) alignment to registration marks, eyelid closure, irrigation, air bubbles, light path interference and tear build-up occurring during the vision correction procedure at the particular time.

2. A method for providing feedback during a vision correction procedure, comprising the steps of:

measuring, in real-time and during the vision correction procedure, aberrations of an optical wavefront from a biological eye with a real-time wavefront sensor;

collecting real-time video movie information, on a frame-by-frame basis of the biological eye with a real-time video camera during the vision correction procedure and while the wavefront sensor is measuring the optical wavefront, with the video movie capturing one or more state(s) of the biological eye including intra ocular lens (IOL) alignment to registration marks, eyelid closure, irrigation, air bubbles, light path interference and tear build-up occurring during the vision correction procedure;

storing, using a computer, measured aberrations of the optical wavefront and collected real-time video information;

synchronizing, using the computer, measured aberrations of the optical wavefront and collected real-time video information;

and simultaneously displaying simultaneously, using the computer, in real-time or in playback mode, aberrations of the optical wavefront measured at a particular time during the vision correction procedure and a frame of the video movie information of the biological eye collected at the particular time during the vision correction procedure to allow correlation of aberrations of optical wavefront data measured at the particular time with one or more state(s) of the biological eye including intra ocular lens (IOL) alignment to registration marks, eyelid closure, irrigation, air bubbles, light path interference and tear build-up occurring during the vision correction procedure at the particular time.

3. The apparatus of claim 1 where the aberrations of the optical wavefront and the frames of the real-time video information of the biological eye are captured and/or recorded in synchronization in a stream manner.

4. The apparatus of claim 1 where the computer is configured to:

convert the aberrations of the wavefront measured by the real-time wavefront sensor into computer graphics which are synchronized and blended with the frames of the video movie information of the biological eye to form a composite movie; and display the composite movie on the display that is synchronized to real-time activity performed during a vision correction procedure.

5. The apparatus of claim 4 where the computer is further configured to allow a user to flip or rotate the composite movie to a preferred orientation.

6. The apparatus of claim 4 where the computer is further configured to allow a user to rewind and replay desired recorded segments of the composite movie on demand during or after the vision correction procedure.

7. The apparatus of claim 1 where the computer is configured to analyze the aberrations of the optical wavefront measured by the real-time wavefront sensor to obtain metrics such as refractive errors and to display the metrics qualitatively and/or quantitatively.

8. The apparatus of claim 7 where the computer is further configured to allow user selection of the manner in which the qualitative and/or quantitative metrics are displayed.

9. The apparatus of claim 8 where the computer is further configured to allow a user to opt for display of refraction versus prescription, and/or positive cylinder versus negative cylinder, and/or end point indicator(s) such as emmetropia.

10. The apparatus of claim 1 where the computer is configured to guide a user in correcting wavefront aberrations/distortions such as refractive errors of the eye in real-time during a vision correction procedure or an examination of the eye.

11. The apparatus of claim 10 where the computer is further configured to guide the user in rotating an implanted toric intraocular lens (IOL) to correct astigmatism.

12. The apparatus of claim 1 where the display is a built-in heads up display.

13. The apparatus of claim 1 where the display is a micro display in the ocular path of a surgical microscope.

14. The apparatus of claim 1 where the display is a number of monitors mutually linked among one another.

15. The apparatus of claim 1 where the computer is configured to analyze the real-time video movie information of the biological eye and/or the aberrations of the optical wavefront measured by the real-time wavefront sensor to determine if the eye is aligned well.

16. The apparatus of claim 1 where the computer is configured to analyze the real-time video movie information of the biological eye and/or the aberrations of the optical wavefront measured by the real-time wavefront sensor to include a directional guide in the display to tell the user which way to move the patient and/or a scope for better alignment.

17. The apparatus of claim 1 where the computer is configured to:

analyze the real-time video movie information of the eye and/or the aberrations of the optical wavefront measured by the real-time wavefront sensor to indicate if the eye lid is closed, or if there is/are air bubble(s) or remains of fractured/ruptured eye lens material inside the eye bag that may affect aberrations of the optical wavefront measurement results; and include confidence indicators in the display to indicate if the wavefront measurement is qualified.

18. The apparatus of claim 1 where the computer is configured to analyze the real-time video movie information of the eye and/or the aberrations of the optical wavefront measured by the real-time wavefront sensor to provide additional information on the state of the eye, such as tear film coverage or dry eye condition and to remind the user to irrigate the eye.

19. An apparatus for providing real-time feedback of the refractive characteristics of a biological subject eye during a vision correction procedure performed on the biological subject eye comprising:

a real-time wavefront sensor configured to perform measurements, in real-time, of aberrations of an optical wavefront returned from the biological subject eye during the vision correction procedure;

a video camera configured to collect real-time video movie information, on a frame-by-frame basis, of the biological subject eye during the vision correction procedure and while the wavefront sensor is measuring the aberrations of the optical wavefront, with the video movie capturing one or more state(s) of the biological subject eye including intra ocular lens (IOL) alignment to registration marks, eyelid closure, irrigation, air bubbles, light path interference and tear build-up occurring during the vision correction procedure; and a computer system, coupled to the real-time wavefront sensor and the real-time video camera, with the computer system configured to store measured aberrations of the optical wavefront and collected real-time video movie information, configured to enable playback of stored aberrations and video movie information and configured to enable simultaneous display, in real-time or in playback mode aberrations of the optical wavefront measured at a particular time during the vision correction procedure and a frame of the video movie information collected at the particular time to allow correlation of aberrations of the optical wavefront measured at the particular time with one or more state(s) of the biological subject eye including intra ocular lens (IOL) alignment to registration marks, eyelid closure, irrigation, air bubbles, light path interference and tear build-up occurring during the vision correction procedure at the particular time.

20. The apparatus of claim 19 further comprising a display, connected to the computer, configured to simultaneously display, in real-time or in playback mode, aberrations of the optical wavefront measured at a particular time during the vision correction procedure and a frame of the video movie information collected at the particular time.

21. The apparatus of claim 20 with the computer further configured to:

convert the aberrations of the optical wavefront measured by the real-time wavefront sensor into computer graphics which are synchronized and blended with the frames of the real-time video movie information to form a composite display and to display a composite movie on the display that is synchronized to real-time activity performed during the vision correction procedure.

22. The apparatus of claim 21 where the computer is further configured to:

record the composite display and configured to allow replay of desired recorded segments of the composite display during or after the vision correction procedure.

23. The apparatus of claim 22 with the computer further configured to:

analyze sampled digitized aberrations of the optical wavefront measured by the real-time wavefront sensor to obtain metrics such as wavefront aberrations/distortions to compute optical refractive errors, typically rendered in a wavefront map and/or units of diopter errors of different orders of wavefront aberrations, to store the metrics using the computer system, and to synchronize the metrics with recorded video image data frames.

24. An apparatus for providing real-time feedback of the refractive characteristics of a biological subject eye during a vision correction procedure performed on the biological subject eye, comprising:

a real-time wavefront sensor configured to perform measurements, in real-time, of aberrations of an optical wavefront returned from the biological subject eye during the vision correction procedure;

a video camera configured to capture/record and to output digital image frames of the biological subject eye during the vision correction procedure while the wavefront sensor is measuring the aberration characteristics during the vision correction procedure, with the digital image frames recording one or more state(s) of the biological subject eye including intra ocular lens (IOL) alignment to registration marks, eyelid closure, irrigation, air bubbles, light path interference and tear build-up occurring during the vision correction procedure; and a computer, coupled to the wavefront sensor and the video camera, with the computer configured to capture/record a frame of aberrations of the optical wavefront measured by the real-time wavefront sensor at a particular time during the vision correction procedure and to synchronize the captured/recorded frame of aberrations measured at the particular time with a digital image frame captured/recorded by the video camera at the particular time to allow comparison of real-time aberrations of the optical wavefront measured at the particular time to one or more state(s) of the biological subject eye including intra ocular lens (IOL) alignment to registration marks, eyelid closure, irrigation, air bubbles, light path interference and tear build-up occurring during the vision correction procedure measured at the particular time and with the computer configured to output frame data including a digital image frame synchronized to a captured/recorded frame of aberrations of the optical wavefront measured at the particular time for display or other purposes.

* * * * *